United States Patent [19]

Marquis et al.

[11] Patent Number: 5,179,214
[45] Date of Patent: Jan. 12, 1993

[54] PROCESS FOR MANUFACTURING ALKYLENE CARBONATES

[75] Inventors: Edward T. Marquis, Austin; John R. Sanderson, Leander, both of Tex.

[73] Assignee: Texaco Chemical Company, White Plains, N.Y.

[21] Appl. No.: 763,729

[22] Filed: Sep. 23, 1991

[51] Int. Cl.$^5$ .................. C07D 317/38; C07D 317/36
[52] U.S. Cl. ..................... 549/230; 549/228; 549/229; 558/260; 558/277
[58] Field of Search ............ 549/228, 229, 230; 558/260, 277

[56] References Cited

U.S. PATENT DOCUMENTS

| | | | |
|---|---|---|---|
| 2,766,258 | 10/1956 | Malkemus | 549/229 |
| 2,773,070 | 12/1956 | Lichtwenwalter | 549/229 |
| 2,873,282 | 2/1959 | McClellan | 549/229 |
| 4,009,183 | 2/1977 | Fumagalli et al. | 549/230 |
| 4,233,221 | 11/1980 | Raines et al. | 549/229 |
| 4,783,445 | 11/1988 | Sun | 528/405 |
| 4,786,741 | 11/1988 | Sachs | 549/230 |
| 4,892,954 | 1/1990 | Brindopke et al. | 549/229 |
| 4,981,948 | 1/1991 | Kawachi et al. | 528/405 |

FOREIGN PATENT DOCUMENTS 0297647 1/1989 European Pat. Off. .
32045 2/1990 Japan .

OTHER PUBLICATIONS

W. J. Peppel, "Preparation and Properties of the Alkylene Carbonates," *Industrial and Engineering Chemistry*, vol. 50, No. 5, pp. 767-770 (May 1958).

Buysch, "Carbon Acid Esters," *Ullmann's Encyclopedia of Industrial Chemistry*, vol. 85, pp. 197-201 (1986).

"Carbonic and Chloroformic Esters," *Kirk-Othmer Encyclopedia of Chemical Technology*, 3rd Edition, pp. 766-770.

Matsuda, et al, "Reaction of Carbon Dioxide with Epoxides in the Presence of Pentavalent Organoantimony Compounds," *Chemistry Letters*, pp. 1261-1262 (1979).

*Primary Examiner*—Cecilia Tsang
*Attorney, Agent, or Firm*—Jack H. Park; Kenneth R. Priem; Russell R. Stolle

[57] ABSTRACT

A method for the manufacture of alkylene carbonates is disclosed. Alkylene carbonates that are free of halogen contaminants are prepared by reacting alkylene oxides and carbon dioxide in the presence of a catalyst selected from the group consisting of cerous acetate, ceric ammonium nitrate, cerous nitrate hexahydrate, and ceric potassium nitrate.

14 Claims, No Drawings

PROCESS FOR MANUFACTURING ALKYLENE CARBONATES

BACKGROUND OF THE INVENTION

1. Field of the Invention

The invention relates to the preparation of alkylene carbonates, also known as glycol carbonates, by reaction of alkylene oxides with carbon dioxide, and more particularly to such processes in which catalysts are employed.

2. Description of Related Methods

The reaction of alkylene oxides with carbon dioxide in the presence of a catalyst is known. U.S. Pat. No. 2,773,070 to Lichtenwalter et al. discloses a process for preparing alkylene carbonates using an ammonium halide catalyst. U.S. Pat. No. 2,873,282 to Mc Clellan discloses the use of certain quaternary ammonium compounds to catalyze the reaction of alkylene oxides and carbon dioxide. W. J. Peppel, in "Preparation and Properties of the Alkylene Carbonates," *Industrial and Engineering Chemistry*, vol. 50, no. 5, pp. 767-770 (May 1958), provides an overview of the various methods then known for the preparation of alkylene carbonates.

It appears that most of the known processes employ halogen-based catalysts. For example, U.S. Pat. No. 4,786,741 to Sachs teaches a process for preparing alkylene carbonates that employs a catalyst selected from the group consisting of organic quaternary ammonium halides, organic quaternary phosphonium halides, organic sulfonium halides, and organic antimony halides. European patent Application 0 297 647 claims a process wherein alkylene carbonates are prepared using a catalyst comprising an alkali or alkaline earth metal halide. Japanese Patent Application Number 63-181765 also discloses a method for the preparation of alkylene carbonates using an alkali halide catalyst. Halide-based catalysts, however, tend to contaminate the alkylene carbonate product with halogen compounds. Other known catalysts may include a strong base that deactivates or decomposes the carbonate. Applicants have discovered that certain cerium salt catalysts provide good yields of alkylene carbonates, and without contaminating the product with halogen compounds.

SUMMARY OF THE INVENTION

The invention concerns a process for the manufacture of alkylene carbonates, comprising reacting an alkylene oxide with carbon dioxide in the presence of a catalyst selected from the group consisting of cerous acetate, ceric ammonium nitrate, cerous nitrate hexahydrate, and ceric potassium nitrate. In another of its aspects, the invention concerns a process for the manufacture of alkylene carbonates, comprising reacting an alkylene oxide having the formula:

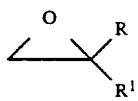

in which R and $R^1$ are selected from the group consisting of hydrogen, aryl groups having from 6 to about 20 carbon atoms, alkyl groups containing from 1 to about 20 carbon atoms, cycloalkyl groups containing from 5 to about 20 carbon atoms, and alkenyl groups containing from 2 to about 20 carbon atoms with (b) carbon dioxide in the presence of a catalyst selected from the group consisting of cerous acetate, ceric ammonium nitrate, cerous nitrate hexahydrate, and ceric potassium nitrate. The invention also concerns a process for preparing alkylene carbonates, comprising reacting (a) an alkylene oxide having the formula:

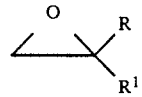

in which R and $R^1$ are selected from the group consisting of hydrogen and alkyl groups containing from 1 to about 5 carbon atoms with (b) a molar excess of carbon dioxide at a temperature of from about 100° to about 225° C. in the presence of a catalyst selected from the group consisting of cerous acetate, ceric ammonium nitrate, cerous nitrate hexahydrate, and ceric potassium nitrate, to obtain an alkylene carbonate product free of halogen contaminants.

DESCRIPTION OF THE PREFERRED EMBODIMENTS

Alkylene oxides that may be employed in the reaction of the present invention include those of the oxirane system. Preferably the alkylene oxide has the following structural formula:

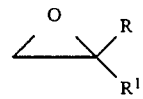

in which R and $R^1$ may be selected from the group consisting of hydrogen, aryl groups having from 6 to about 20 carbon atoms, alkyl groups containing from 1 to about 20 carbon atoms, cycloalkyl groups containing from 5 to about 20 carbon atoms, and alkenyl groups containing from 2 to about 20 carbon atoms. Preferably, R and $R^1$ are selected from the group consisting of hydrogen, aryl groups having from 6 to about 12 carbon atoms, alkyl groups containing from 1 to about 5 carbon atoms, cycloalkyl groups containing from 5 to about 12 carbon atoms, and alkenyl groups containing from 2 to about 5 carbon atoms. More preferably, R and $R^1$ are selected from the group consisting of hydrogen, alkyl groups containing from 1 to about 5 carbon atoms, and alkenyl groups containing from 2 to about 5 carbon atoms. Especially preferred are ethylene oxide and propylene oxide. The oxirane compounds, as shown by the formula above, have the ring oxygen atom attached to two adjacent carbon atoms.

The reaction may be carried out at a temperature of from about 100° to about 225° C., preferably from about 175° to about 215° C. The reaction may be carried out at atmospheric pressure or, preferably, under a pressure of about 300 psig or greater. More preferably, the reaction is carried out under a pressure of about 1000 to about 2000 psig. The reaction may be conducted either batchwise or continuously.

In a continuous reaction, alkylene oxide and carbon dioxide are introduced to a continuous reactor containing the catalyst, from which a portion of the reaction mixture may be continuously recirculated through the reactor. Another portion of this reaction mixture is continuously withdrawn and flashed to remove unreacted carbon dioxide and alkylene oxide, which are compressed and returned to the reactor. The residue from the flashing treatment is subjected to distillation to separate the alkylene carbonate from the catalyst solution. Residual catalyst solution or slurry (bottoms) may be returned directly to the reactor. At times, it may be desirable to discard a portion of the recovered catalyst stream to prevent accumulation of unwanted by-products in the catalyst stream.

Alternatively, batches of alkylene oxide and catalyst may be introduced into an autoclave or kettle type reactor. The desired pressure may be built up by introducing carbon dioxide. Typically, the reaction mixture is heated to reaction temperature, agitated, and held under a superatmospheric pressure of carbon dioxide.

The alkylene oxide and carbon dioxide should be mixed in proportion to provide an excess of carbon dioxide over and above the stoichiometric amount required for reaction. This excess may be of the order of from about 1% to about 500% by weight. An excess of alkylene oxide should be avoided because it results in undesired by-products, chiefly alkylene oxide polymers, and because explosive conditions may result.

Catalysts useful in the present invention are cerium salts selected from the group consisting of cerous acetate, ceric ammonium nitrate, cerous nitrate hexahydrate, and ceric potassium nitrate. Especially preferred are cerous acetate and cerous nitrate hexahydrate. Surprisingly, the following were found to provide very poor yields: ceric ammonium sulfate, cerous carbonate, cerous oxalate, ceric oxide, ceric potassium nitrate on AW300 molecular sieves, ceric potassium nitrate on 13X molecular sieves, cerous sulphate, and cerium (III) nitrate deposited on Engelhard Clay Grade-13.

The amount of catalyst used should be from about 0.1% to about 10%, preferably from about 1% to about 5%, based on the weight of the reaction mixture. In general, the greater the catalyst concentration, within these limits, the more rapid and complete the reaction.

The invention will be further illustrated by the following examples, which are given by way of illustration and not as limitations on the scope of this invention. The entire text of every patent, patent application or other reference mentioned above is hereby incorporated herein by reference.

EXAMPLES

Example 1

To a clean, dry, 1-liter 316 stainless steel autoclave were added 150.0 g of propylene oxide (2.58-moles) and 8.0 g of ceric ammonium nitrate [$Ce(NH_4)_2(NO_3)_6$, Alfa]. The clave was purged with carbon dioxide and then 185.0 g (4.20 moles) of carbon dioxide were added at room temperature. The reaction mixture was heated to 180° C. and held at 180° C. for 2.0 hours before cooling to ambient temperature. The product weighed 155.5 g. After filtration, the weight of the filtrate was 137.0 g. Gas chromatography indicated the presence of 51.38% propylene carbonate in the filtrate (70.389 g PC or 0.69 moles PC). The yield of propylene carbonate was 26.70% without optimized reaction conditions. The filtrate contained <50 ppm cerium (by atomic absorption spectroscopy.)

Example 2

In an experiment identical to Example 1 above, except that 8.0 g of ceric potassium nitrate [$Ce(K)_2(NO_3)_6$, Pfaltz & Bauer) was used as catalyst, the filtrate contained 57.7% propylene carbonate (Yield of PC=33.1%).

Example 3

In an experiment identical to Example 1 above, except that 8.0 g of cerous nitrate hexahydrate [$Ce(NO_3)_3.6H_2O$, Pfaltz & Bauer] was used as catalyst, the filtrate contained 87.03% propylene carbonate (Yield of PC =61.8%).

Examples 4 & 5

When the catalysts were ceric oxide and ceric ammonium sulfate and the same reaction procedure as described in Example 1 was employed, the yields of propylene carbonate were 0.86% and 3.26%, respectively.

TABLE I

| EX. NO. | CATALYST | GRAMS PRODUCED | GRAMS AFTER FILTRATION | GC AREA % PC | YIELD PC (%) |
|---|---|---|---|---|---|
| 1 | Ceric Ammonium Nitrate[1] | 155.5 | 137.0 | 51.38 | 26.70 |
| 2 | Ceric Potassium Nitrate[2] | 159.1 | 151.3 | 57.69 | 33.11 |
| 3 | Cerous Nitrate Hexahydrate[3] | 206.4 | 193.6 | 84.20 | 61.82 |
| 4 | Ceric Oxide[4] | 137.9 | 121.6 | 1.86 | 0.86 |
| 5 | Ceric Ammonium Sulfate[5] | 147.0 | 136.0 | 6.33 | 3.26 |
| 6 | Cerous Acetate[6] | 211.9 | 165.7 | 84.85 | 53.33 |
| 7 | Cerous Carbonate[7] | 135.0 | 16.5 | 32.88 | 2.06 |
| 8 | Cerous Oxalate[8] | 136.2 | 106.9 | 10.28 | 4.17 |
| 9 | Cerous Phosphate[9] | 143.8 | PRODUCT IS RUBBERY | | |
| 10 | Ceric Potassium Nitrate[10] | 133.5 | 38.2 | 8.50 | 1.23 |
| 11 | Ceric Potassium Nitrate[11] | 136.9 | 94.6 | 5.73 | 2.06 |
| 12 | Cerous Sulfate[12] | 133.9 | 108.2 | 0.70 | 0.29 |
| 13 | Cerium/Clay-13 Catalyst[13] | 150.9 | 127.5 | 3.08 | 1.49 |

[1]$Ce(NH_4)_2(NO_3)_6$(Alfa Chemical) Mol. Wt. 548.24; % Ce = 25.56
[2]$Ce(K)_2(NO_3)_6$ (Pfaltz & Bauer) Mol. Wt. 590.53; % Ce = 23.73
[3]$Ce(NO_3)_3(H_2O)_6$ (Pfaltz & Bauer) Mol. Wt. 434.24; % Ce = 32.27
[4]$CeO_2$ (Alfa)
[5]$Ce(NH_4)_4(SO_4)_4 (H_2O)_2$ (Pfaltz & Bauer) Mol. Wt. 632.56; % Ce = 22.15
[6]$Ce(C_2H_3O_2)_3$ $XH_2O$ (Pfaltz & Bauer)
[7]$Ce_2(CO_3)_3$3 $XH_2O$ (Aldrich)
[8]$Ce_2(C_2O_4)_3$ (Aldrich)
[9]$CePO_4$ (Pfaltz & Bauer)
[10]On AW 300 molecular sieves (2.5% K, 1.0% Ce)
[11]On 13X molecular sieves (1.9% K, 0.6% Ce)
[12]$Ce_2(SO_4)_3$ (Aldrich)
[13]Engelhard Clay Grade-13 impregnated with CE(III) Nitrate (0.38% Ce)

We claim:

1. A process for the manufacture of alkylene carbonates, comprising reacting an alkylene oxide having the formula:

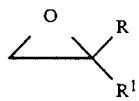

in which R and R¹ are selected from the group consisting of hydrogen, alkyl groups containing from 1 to 20 carbon atoms, and alkenyl groups containing from 2 to 20 carbon atoms with (b) carbon dioxide in the presence of a catalyst selected from the group consisting of cerous acetate, ceric ammonium nitrate, cerous nitrate hexahydrate, and ceric potassium nitrate.

2. The process of claim 1, in which the catalyst is selected from the group consisting of cerous acetate and cerous nitrate hexahydrate.

3. The process of claim 1, in which the catalyst is cerous acetate.

4. The process of claim 1, in which the catalyst is cerous nitrate hexahydrate.

5. The process of claim 1, in which the alkylene oxide and carbon dioxide are reacted at a temperature of from about 100° to about 225° C.

6. The process of claim 1, in which the alkylene oxide and carbon dioxide are reacted at a temperature of from about 175° to about 215° C. and at a pressure of from about 300 to about 2000 psig.

7. The process of claim 1, in which the catalyst is selected from the group consisting of cerous acetate and cerous nitrate hexahydrate, and in which the alkylene oxide and carbon dioxide are reacted at a temperature of from about 175° to about 215° C. and at a pressure greater than about 300 psig.

8. A process for preparing alkylene carbonates, comprising reacting (a) an alkylene oxide having the formula:

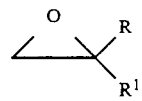

in which R and R¹ are selected from the group consisting of hydrogen and alkyl groups containing from 1 to 5 carbon atoms with (b) a molar excess of carbon dioxide at a temperature of from about 100° to about 225° C. in the presence of a catalyst selected from the group consisting of cerous acetate, ceric ammonium nitrate, cerous nitrate hexahydrate, and ceric potassium nitrate.

9. The process of claim 8, in which the catalyst is selected from the group consisting of cerous acetate and cerous nitrate hexahydrate.

10. The process of claim 8, in which the catalyst is cerous acetate.

11. The process of claim 8, in which the catalyst is cerous nitrate hexahydrate.

12. The process of claim 8, in which the alkylene oxide and carbon dioxide are reacted at a temperature of from about 175° to about 215° C. and at a pressure greater than about 300 psig.

13. The process of claim 8, in which the catalyst is selected from the group consisting of cerous acetate and cerous nitrate hexahydrate, and in which the alkylene oxide and carbon dioxide are reacted at a temperature of from about 175° to about 215° C. and at a pressure greater than about 300 psig.

14. A process for preparing alkylene carbonates, comprising reacting (a) ethylene oxide or propylene oxide with (b) a molar excess of carbon dioxide, at a temperature of from about 175° to about 215° C. and at a pressure greater than about 300 psig, in the presence of a catalyst selected from the group consisting of cerous acetate and cerous nitrate hexahydrate.

* * * * *